United States Patent
March (10) Patent No.: US 7,128,916 B2
(45) Date of Patent: Oct. 31, 2006

(54) BACTERIOPHAGE-MEDIATED IMMUNISATION

(75) Inventor: John Bernard March, Midlothian (GB)

(73) Assignee: Moredun Research Institute, Midlothian (GB)

( * ) Notice: Subject to any disclaimer, the term of this patent is extended or adjusted under 35 U.S.C. 154(b) by 0 days.

(21) Appl. No.: 10/473,664

(22) PCT Filed: Mar. 25, 2002

(86) PCT No.: PCT/GB02/01413

§ 371 (c)(1), (2), (4) Date: Sep. 17, 2003

(87) PCT Pub. No.: WO02/076498

PCT Pub. Date: Oct. 3, 2002

(65) Prior Publication Data

US 2004/0121974 A1 Jun. 24, 2004

(30) Foreign Application Priority Data

Mar. 23, 2001 (GB) ................. 0107319.6

(51) Int. Cl.
*A61K 39/12* (2006.01)
*A61K 35/76* (2006.01)
*A61K 48/00* (2006.01)
*A61K 45/00* (2006.01)

(52) U.S. Cl. ............... 424/199.1; 424/93.2; 514/44
(58) Field of Classification Search ............ 514/44; 424/199.1, 93.2, 93.6; 435/235.1, 320.1, 435/456
See application file for complete search history.

(56) References Cited

U.S. PATENT DOCUMENTS

| 5,736,388 A | 4/1998 | Chada et al. | |
|---|---|---|---|
| 6,054,312 A | 4/2000 | Larocca et al. | |
| 2003/0113293 A1* | 6/2003 | Bermudes et al. | 424/93.2 |

FOREIGN PATENT DOCUMENTS

| WO | WO 9805344 | 2/1998 |
|---|---|---|
| WO | WO 9910014 | 3/1999 |
| WO | WO99/055720 A1 | 11/1999 |

OTHER PUBLICATIONS

Horst et al PNAS 72:3531-3535, 1975.*
Bastien et al (Virology 234:118-122, 1997).*
Douglas, R.G. Transactions of the American Clinical and Climatological Association 109: 185-198, 1998.*
Aujame et al. "Experimental Design Optimization of Filamentous Phage Transfection into Mammalian Cells by Cationic Lipids", *Biotechniques* 28:1202-1213 (2000).
Horst et al. "Gene transfer to human cells: Transducing phage λplac gene expression in $GM_1$-gangliosidosis fibrosis", *Proc. Natl. Acad. Sci.* 72:3531-3535 (1975).
Okayama et al. "Bacteriophage Lambda Vector for Transducing a cDNA Clone Library into Mammalian Cells", *Molec. and Cell. Biol.* 5:1136-1142 (1985).
Srivatsan et al. "Plasmid, phage, and genomic DNA-mediated transfer and expression of prokaryotic and eukaryotic genes in cultured human cells", *Cytogenet. Cell Genet.* 38:227-234 (1984).
Bastien, N., et al. "Protective Immune Responses Induced by the Immunization of Mice with a Recombinant Bacteriophage Displaying a Epitope of the Human Respiratory Syncytial Virus" *Virology* 234:118-122 (1997).
De Berardinis, P., et al. "Phage Display of Peptide Epitopes From HIV-1 Elicits Strong Cytolytic Response" *Nature Biotechnology* 18:2000.
Gaubin, M., et al. "Processing of Filamentous Bacteriophage Virions in Antigen-Presenting Cells Targets Both HLA Class I and Class II Peptide Loading Compartments" *DNA and Cell Biology* 22(1):11-18 (2003).
International Search Report corresponding to PCT/GB02/01413. Mailed Jun. 13, 2003.
Ishiura, M., et al. "Phage Particle-Mediated Gene Transfer to Cultured Mammalian Cells" *Molecular and Cellular Biology* 2(6):607-616 (Jun. 1982).
Monahan, S.J., et al. "Viral Vectors for Gene Transfer into Antigen Presenting Cells" *Molecular Therapeutics* 1(5):558-564 (1999).
Vincent, J.A., et al. "An In Vitro, Complement-Dependent Model of Particle Transfer From Erythrocytes to Macrophages" *Immunopharmacology* 49(1-2):90 (Aug. 2000).
De Berardinis, P., et al. "Phage Display of Peptide Epitopes From HIV-1 Elicits Strong Cytolytic Response" *Nature Biotechnology*, 18:873-876 (2000).

* cited by examiner

Primary Examiner—Mary E. Mosher
(74) Attorney, Agent, or Firm—Myers Bigel Sibley & Sajovec, PA (57) ABSTRACT

The present invention relates to vaccines comprising a bacteriophage which has been engineered to express an immunogenic protein/peptide and wherein the surface of the bacteriophage has not been modified to contain proteins/peptides designed to target the phage to receptors on the surface of specific cell types.

18 Claims, 7 Drawing Sheets

FIGURE 1

(Moredun Research Institute)

Antibody responses in mice vaccinated with DNA vaccine

Figure 1:
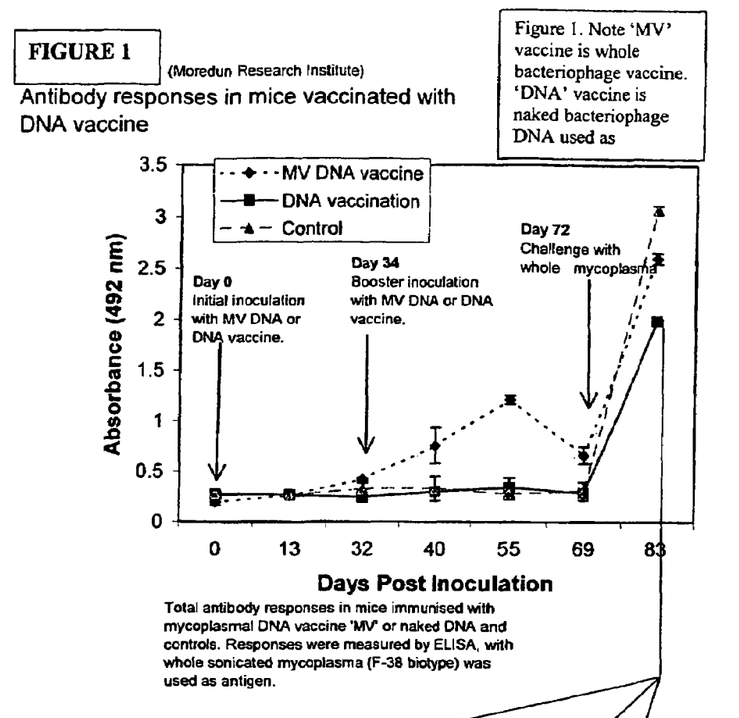
FIG. 1 shows the antibody responses in mice vaccinated with the bacteriophage based vaccine of the present invention, as compared to conventional intro-muscular DNA vaccination and a control.

Figure 1. Note 'MV' vaccine is whole bacteriophage vaccine. 'DNA' vaccine is naked bacteriophage DNA used as Total antibody responses in mice immunised with mycoplasmal DNA vaccine 'MV' or naked DNA and controls. Responses were measured by ELISA, with whole sonicated mycoplasma (F-38 biotype) was used as antigen.

FIGURE 2

Immunoglobulin subtype following whole organism immunisation

Figure 2:
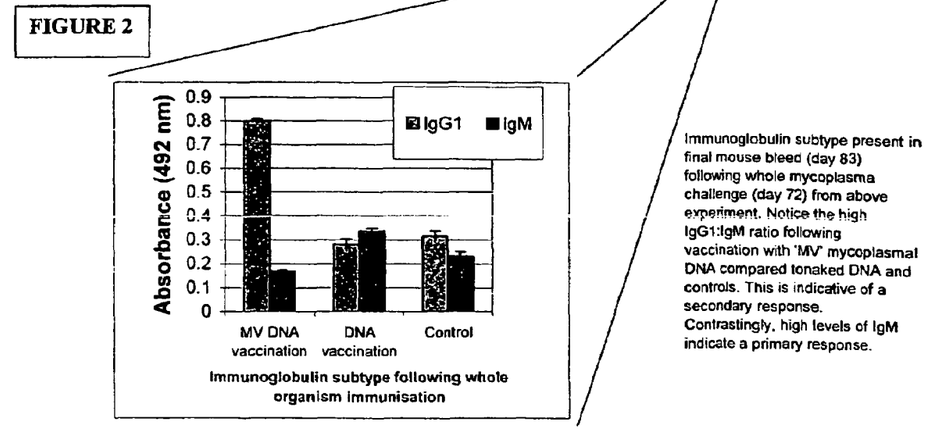
FIG. 2 shows the relative amounts of IgG and IgM produced by the vaccinated mice.

Immunoglobulin subtype present in final mouse bleed (day 83) following whole mycoplasma challenge (day 72) from above experiment. Notice the high IgG1:IgM ratio following vaccination with 'MV' mycoplasmal DNA compared to naked DNA and controls. This is indicative of a secondary response. Contrastingly, high levels of IgM indicate a primary response.

Figure 3:
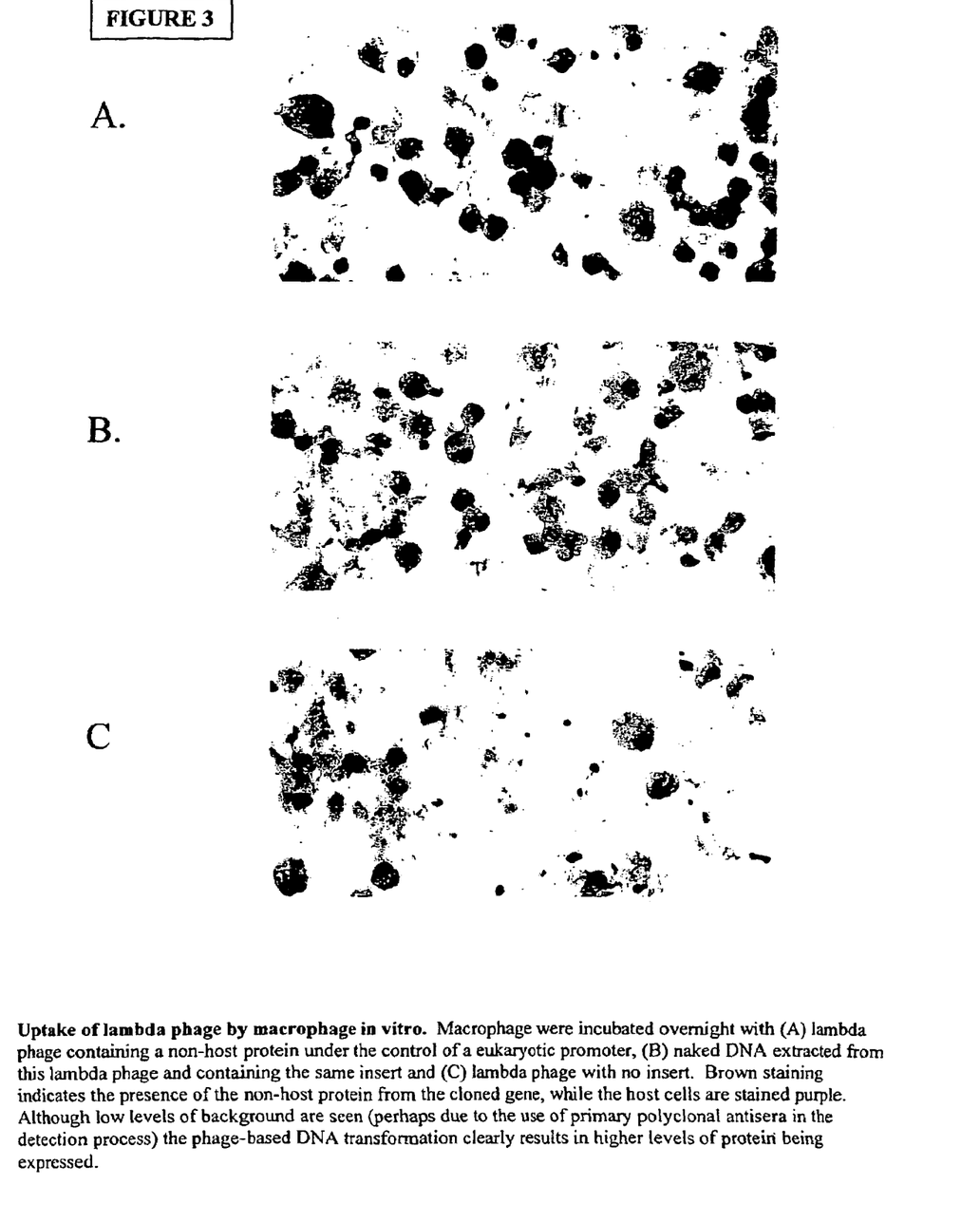
FIG. 3 shows the uptake and expression of foreign DNA by macrophages in vitro.
Figure 4:
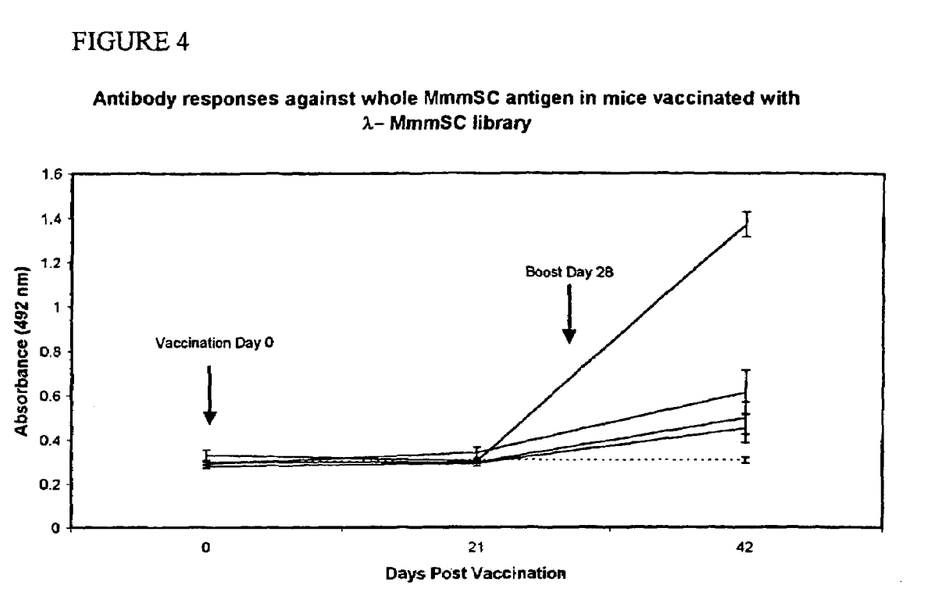
FIG. 4 shows antibody responses against whole MmmSC antigen in mice vaccinate with λ-MmmSC library. Total antibody responses against MmmSC sonicated whole cell extracts from mice vaccinated with lambda MmmSC expression library (λMmmSC). Responses were measured by ELISA. The responses from four mice vaccinated with λMmmSC are shown by unbroken lines. A representative response from a control mouse is shown by a dotted line. Times of vaccination are shown by the arrows (day 0 and day 28)
Figure 5:
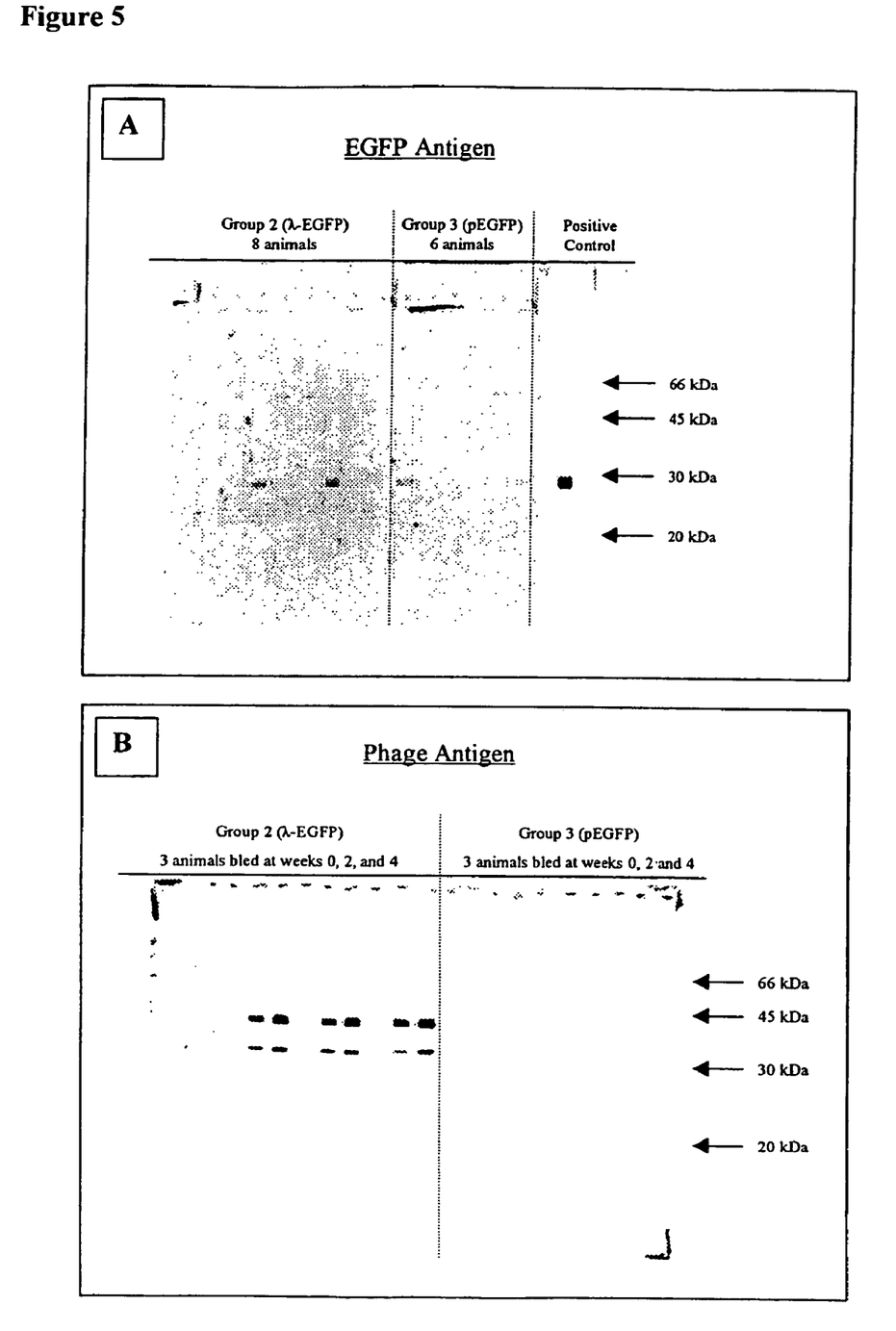
FIG. 5 shows (A) Immunoblot of purified GFP probed with final bleeds from mice immunised with λ-GFP (left; 8 lanes, 1 per mouse), plasmid pEGFP-C1 (middle; 6 lanes, 1 per mouse), and positive control (rabbit anti-GFP). The remaining two mice vaccinated with pEGFP-C1 were tested on a different immunoblot and did not reveal a response against pure GFP. (B) Immunoblot against λ proteins with time course sera from 3 representative animals vaccinated with λ-GFP (left) or pEGFP-C1 (right)

Uptake of lambda phage by macrophage in vitro. Macrophage were incubated overnight with (A) lambda phage containing a non-host protein under the control of a eukaryotic promoter, (B) naked DNA extracted from this lambda phage and containing the same insert and (C) lambda phage with no insert. Brown staining indicates the presence of the non-host protein from the cloned gene, while the host cells are stained purple. Although low levels of background are seen (perhaps due to the use of primary polyclonal antisera in the detection process) the phage-based DNA transformation clearly results in higher levels of protein being expressed.

FIGURE 4

Antibody responses against whole MmmSC antigen in mice vaccinated with λ- MmmSC library

Figure 5

Figure 6A:
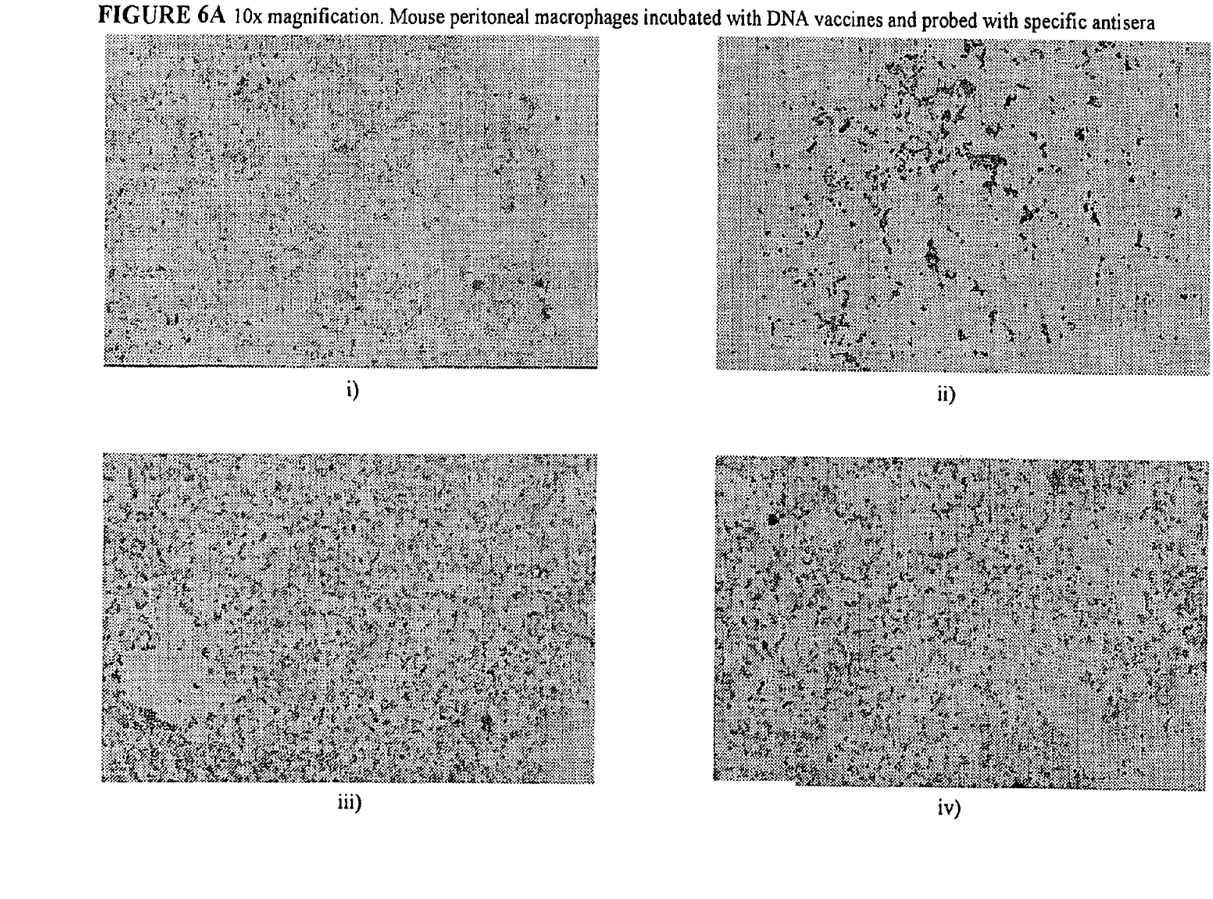
FIG. 6 shows mouse peritoneal macrophages incubated with DNA vaccines and probed with specific antisera: A, ×10 magnification; B, 40× magnification: i) no vaccine. Probed with anti-GFP; ii) incubated with λB1 (MmmSC pdh gene) and probed with anti-MmmSC IgG; iii) incubated with λ-GFP and probed with anti-GFP; and iv) incubated with plasmid pEGFP and probed with anti-EGFP.

FIGURE 6A 10x magnification. Mouse peritoneal macrophages incubated with DNA vaccines and probed with specific antisera FIGURE 6B 40x magnification. Mouse peritoneal macrophages incubated with DNA vaccines and probed with specific antisera

Figure 7

BACTERIOPHAGE-MEDIATED IMMUNISATION

RELATED APPLICATIONS

This application claims priority under 35 U.S.C. § 371 from PCT Application No. PCT/GB02/01413, filed in English on Mar. 25, 2002, which claims the benefit of Great Britain Application Serial No. 0107319.6 filed on Mar. 23, 2001, the disclosures and contents of which are incorporated by reference herein in their entireties.

The present invention relates to vaccines comprising a bacteriophage engineered to express an immunogenic protein/peptide.

Genetic vaccination is a new and exciting technology in which nucleic acid is used as the vaccine material (for review see Leitner et al. 2000. Vaccine 18: 765–777). In contrast, traditional vaccines require the use of pathogenic microbes or their antigenic components. There are three classes of "traditional" vaccines: attenuated, killed/subunit, and recombinant. Attenuated vaccines are live microorganisms with reduced pathogenicity and are generally the most effective vaccines. However, they can produce complications if the vaccine agent grows unchecked or reverts to a more pathogenic form. Killed or subunit vaccines require multiple injections, thereby increasing cost and creating logistical problems, and may contain incompletely killed microbes. Recombinant vaccines, in which an antigen from a pathogenic organism is engineered into a non-pathogenic vector can be effective, but difficulties in achieving expression of the antigen in a native conformation often limit efficacy.

To be effective, vaccines need to provide a sufficient dose of antigen for time periods long enough to induce a secondary (memory) response. This poses a problem for traditional vaccines; DNA/RNA vaccines, however, can effectively produce copies of pathogenic antigens for long periods of time, and thus induce both MHC Class I & II responses, as seen with live vaccines. However, for all their promise, DNA vaccines have yet to fulfil their full potential. Despite eliciting a measurable humoral (antibody) immune response, many DNA vaccines exhibit poor efficacy when challenged with the infective organism (Beard, C W & Mason, P W. 1998. Nature Biotech. 16: 1325).

The mechanism by which the nucleic acid enters host cells and induces an immune response is unclear at present. The simplest technique is to administer the DNA as a soluble injection, usually given intramuscularly. Two other techniques in common use are "gene gun" technology, in which DNA is precipitated onto tiny gold particles which are forced into cells with a helium blast, or liposome-mediated transfection, in which DNA is coated with positively charged lipid to form a complex which fuses with the host cell membrane. It is believed that cells surrounding the immunisation site take up the DNA, express the encoded antigen(s), and are recognised as "foreign" by antigen presenting (AP) cells of the immune system, which then proceed to activate T and B cells to elicit an immune response against the antigen.

Limitations would appear to be: (1) Expression is relatively inefficient and non-specific, with the majority of the DNA being expressed in non-AP cells; (2) Expression of foreign antigens in non AP-cells will eventually lead to the death of that cell due to its recognition as being "infected" by the host immune system, thus shortening the potential immune response; and (3) Naked DNA/RNA is highly sensitive to the action of nucleases. It is likely that the majority of nucleic acid used for immunisation is degraded shortly following immunisation.

WO98/05344 describes a method for delivering exogenous genes using a bacteriophage vector wherein the bacteriophage vector has been modified to include on its surface a ligand that binds to a receptor on a target cell. The vectors described are generally intended to be used for gene therapy applications where the vectors are targeted to specific cell types. There is also mention of using the modified bacteriophage vectors to deliver antigenic peptides.

U.S. Pat. No. 5,736,388 describes modified lamboid bacteriophage for delivering nucleic acid molecules to eukaryotic cells in which the bacteriophage has been modified by incorporating mutant tail fibre proteins or by incorporating ligands for eukaryotic cell receptors.

U.S. Pat. No. 6,054,312 relates to filamentous phage particles displaying a ligand on their surface, the ligand being a fusion protein with a phage capsid protein, covalently conjugated to phage particles, or complexed with modified phage particles.

WO99/55720 also describes phage which have been modified to externally display a heterologous targeting protein for use in targeted gene delivery.

However, the aforementioned patents/patent applications all describe modifying the surface of the phage so as allow targeted delivery of nucleic acid to specific cells, generally for gene therapy purposes.

A number of documents (Ishiura, M. et al, Molec. And Cell. Biol., p607–616, 1982; Aujame, L. et al, Biotechiques, 28 p1202–1213, 2000; Horst, J. et al, Proc. Natl. Acad. Sci., 72, p3531–3535, 1975; Jkayama and Dery, Molec. and Cell. Biol. 5, p1136–1142, 1985; and Srivatsan, E. et al, 38, p227–234, 1984) relate to the use of phage to transfect cultured mammalian cells and express protein therein. However, there is no suggestion that this could be applied in vivo, or used in the development of vaccines.

It is an object of the present invention to obviate and/or mitigate at least one of the aforementioned disadvantages.

In a first aspect the present invention provides a vaccine formulation comprising a bacteriophage particle the surface of which is unmodified and a pharmaceutically acceptable carrier therefor, the bacteriophage particle comprising an exogenous nucleic acid molecule encoding a polypeptide which is capable of expression and presentation on the surface of an antigen presenting cell of an organism, such that an immune response to said polypeptide is raised in the organism.

Unlike previous disclosures, see for example WO98/05344, U.S. Pat. No. 5,736,388, U.S. Pat. No. 6,054,312 and WO99/55720, it is to be appreciated that the surface bacteriophage of the present invention has not been modified to comprise exogenous peptides/proteins (ie. peptides/proteins not normally present) on the surface of the phage, designed to target the phage to receptors on the surface of specific cell types. It is to be understood therefore that the surface of the bacteriophage may be modified to comprise exogenous peptides/proteins not designed to target the phage to receptors on the surface of specific cell types.

The present inventors have observed that bacteriophage which have not been modified to comprise targeting peptides or ligands on the surface of the bacteriophage particle are taken up by AP cells. Thus, the bacteriophage of the present invention are thought to be recognised as "foreign" and are therefore processed in the normal manner by a host's immune system. Moreover, by modifying the genome of the bacteriophage to include exogenous nucleic acid capable of encoding a foreign peptide/protein, that is a peptide/protein not normally present in a chosen mammalian host, an immune response to this foreign protein is elicited. Thus, the nucleic acid encoding the foreign peptide/protein is expressed (in an antigen present cell or otherwise) and presented on the surface of the AP cell. It is to be appreciated that the immune response may be a humoral (ie. antibody) and/or cellular immune response.

Exogenous nucleic acid relates to a non-naturally occurring polynucleotide that is capable of being expressed as an heterologous peptide or protein, that is a peptide or protein which is not normally expressed or is expressed at biologically insignificant levels in a naturally-occurring bacteriophage. The expressed peptide or protein is expressed at a level sufficient to elicit an immune response in a host to which the vaccine has been presented.

It is to be appreciated that the present invention is applicable to the preparation of a vaccine for practically any infectious disease, providing that a suitable immuno-protective response can be raised to a protein or proteins of an infectious agent. Examples of suitable diseases include vaccination directly against the disease-causing agent, or alternatively, vaccination against the disease-carrying vector. Such infectious agents or vectors include virus, bacteria, fungi, yeast, protozoa, helminths, insecta, and transmissible spongiform encephalopathies. The present invention would be applicable to infectious diseases of both humans and animals. Lists of suitable diseases are well known to those versed in the art and examples are to be found in the O.I.E. Manual of Standards and Diagnostic Tests 3rd Ed., OIE, Paris 1996, Topley & Wilson's Principles of Bacteriology, Virology and Immunity 8th Ed., Eds. Parker M. T. and Collier L. H., Vol IV (Index), Edward Arnold, London 1990, The Zoonoses: Infections Transmitted from Animals to Man. Bell J. C. et al., Edward Arnold, London 1988 and Parasitology: The Biology of Animal Parasites 6th Ed. Noble E. R. et al., Lea & Febiger, Philadelphia, 1989. In addition the present invention could be used to elicit an immune response against cancer cells by means of the expression of a cancer cell specific antigen as the vaccine protein.

The present invention thus provides a way of encapsulating exogenous nucleic acid eg. DNA inside a stable matrix, in order to protect it from for example nucleases present for example in cells. The "foreign" proteins on the surface of the bacteriophage allow direct uptake of nucleic acid specifically to antigen presenting (AP) cells. Without being bound by theory it is expected the bacteriophage particle is recognised as a foreign antigen. The entire particle is thus taken up directly by the antigen presenting cells of the host immune system, where the protein coat is removed, releasing the DNA which may then move into the nucleus and be expressed. This procedure, is thought to be efficient, since vaccine DNA expression and subsequent polypeptide production should only take place in AP cells; the optimum route for inducing an immune response.

In general the term "polypeptide" refers to a chain or sequence of amino acids displaying an antigenic activity and does not refer to a specific length of the product as such. The polypeptide if required, can be modified in vivo and/or in vitro, for example by glycosylation, amidation, carboxylation, phosphorylation and/or post translational cleavage, thus inter alia, peptides, oligo-peptides, proteins and fusion proteins are encompassed thereby. Naturally the skilled addressee will appreciate that a modified polypeptide should retain physiological function i.e. be capable of eliciting an immune response.

The bacteriophage of the present invention preferably contain appropriate transcription/translation regulators such as promoters, enhancers, terminators and/or the like. Typically the promoter may be a eukaryotic promoter such as CMV, SV40, thymidine kinase, RSV promoter or the like. Conveniently the promoter may be a constitutive promoter. However, controllable promoters known to those of skill in the art may also be used. For example constructs may be designed which comprise the exogenous nucleic acid under control of a constitutive promoter and a controllable promoter. In this manner it may be possible to cause expression of the exogenous nucleic acid initially by way of the constitutive promoter and at a second time point by expression from the controllable promoter. This may result in a stronger immune response.

Many suitable bacteriophage are known to those skilled in the art. An example of a suitable bacteriophage is lambda (λ). Currently, bacteriophage λ is used as a cloning vector during routine DNA manipulation procedures. For these, the DNA is purified away from the phage structure. However, an intact λ phage particle fulfils the criteria listed above; the DNA is contained within a protective protein matrix which is recognised as a foreign antigen by the host immune system. Phage λ normally infects the bacterium $E.$ $coli$, and its DNA is thought to be "inert" in a eukaryotic cell (ie. it will not be expressed). However, if a eukaryotic promoter is incorporated upstream of the vaccine (or foreign) gene of interest, then expression of that gene to provide an antigen ie. protein/peptide should occur if the DNA is taken up by a mammalian cell. Due to extensive use as a routine cloning vector, many variants of λ exist, including some with strong eukaryotic promoters designed to direct expression in mammalian cells. Normally, the relevant section of the λ vector is removed as plasmid DNA prior to further genetic manipulations:—highly purified plasmid DNA from an $E.$ $coli$ host will then be used for genetic immunisation. However, if an intact λ phage particle containing a eukaryotic promoter and the vaccine (ie. exogenous) gene of interest is used for immunisation, it is taken up by AP cells. Following protein coat removal, antigen production directly within the AP cell is thought to occur and antigen presented on the surface of the AP cells so as to induce an immune response. In this case only the most basic purification procedure is required to produce phage particles ready for immunisation. An additional advantage of using λ compared to plasmid cloning vectors is that much larger insert sizes can be accommodated.

Other suitable bacteriophage are well known to those of skill in the art and include p1 phage, T phages (eg. T1–7), Mu, fd or M13, as well as filamentous phage.

Preferred bacteriophage of the present invention have the ability to incorporate exogenous nucleic acid and associated promoters, enhancers, terminators and/or the like of between about 0.5–100 kilobases. For example known lambda phages can accommodate between 9–50 kilobases. In this manner it is possible to express single or multiple copies of a peptide/protein or a plurality of peptides/proteins.

Typically, the bacteriophage of the present invention are abortive to lytic growth in the natural bacterial flora of the chosen mammalian host. Many "laboratory" strains of phage are known for example which are only able to infect non-wild type "laboratory" bacterial strains. Additionally or alternatively the bacteriophage may be abortive to lytic growth of the host bacterial strain in vitro, or require helper phage to grow in vitro. Thus the bacteriophage may contain for example an amber mutation, a temperature sensitive mutation or the like.

Means are generally provided to enhance expression of the exogenous nucleic acid in the AP cells. Such means include methods to help minimise nucleic acid degradation and/or targeting to the nucleus. Examples of such means include the use of chloroquine or other inhibitors of lysosomal/endosomal enzymic catabolism to minimise nucleic acid degradation and/or the use of nuclear localisation signals to direct the nucleic acid to the nucleus.

The vaccine formulation may further comprise a source of the protein which is to be expressed by the bacteriophage. In this manner a host may elicit a primary immune response to the protein and thereafter elicit a further or sustained immune response due to the protein being expressed and presented on the surface of an AP cell.

In a further embodiment the phage could be modified to also express the antigenic protein on the surface of the phage particle. For example it is possible to use intact bacteriophage M13 particles as a vector vehicle. Insert sizes for M13 are considerably smaller than for λ, but the use of "Phage Display" technology (Hawkins, R E et al. 1992, J. Mol. Biol. 226: 889) means that the phage particle can carry a portion of foreign antigen fused to its coat protein. Thus a construct can be made in which the vaccine gene is under control of both a prokaryotic (eg. Lac Z promoter) and a eukaryotic promoter (eg. CMV promoter): when grown in an E. coli host, the prokaryotic promoter will direct expression of the vaccine antigen and allow its incorporation into the M13 coat as a protein conjugate, which should elicit a strong primary response following vaccination. Thereafter, following uptake by AP cells, the DNA will be released and the eukaryotic promoter will direct long-lasting expression of the vaccine antigen from within the AP cell, maintaining a strong secondary response.

The exogenous nucleic acid may encode at least a further polypeptide(s), such as a polypeptide capable of augmenting the immune response. The further polypeptide may be an adjuvant protein or polypeptide, such as a cytokine coding, for example, for an interferon such as γ interferon (γIFN), IL-2, IL-6, IL-7, IL-12, CM-CSF and/or other cytokines/chemokines. Moreover, "helper epitopes", such as HepB core antigen may be used to activate B cells and elicit strong T-cell responses. Alternatively or additionally, immunostimulatory signals such as CpG oligodinucleotides may be used.

The bacteriophage may be administered by any suitable route, for example by injection and may be prepared in unit dosage in for example ampules, or in multidose containers. The bacteriophage may be present in such forms as suspensions, solutions, or emulsions in oily or preferably aqueous carriers. Alternatively, the bacteriophage may be in lyophilized form for reconstitution, at the time of delivery, with a suitable carrier, such as sterile pyrogen-free water. In this manner stabilising agents, such as proteins, sugars etc. may be added when lyophilising the phage particles. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of bacteriophage material.

In a preferred presentation, the vaccine can also comprise an adjuvant. Adjuvants in general comprise substances that boost the immune response of the host in a non-specific manner. A number of different adjuvants are known in the art. Examples of adjuvants may include Freund's Complete adjuvant, Freund's Incomplete adjuvant, liposomes, and niosomes as described, for example, in WO 90/11092, mineral and non-mineral oil-based water-in-oil emulsion adjuvants, cytokines, short immunostimulatory polynucleotide sequences, for example in plasmid DNA containing CpG dinucleotides such as those described by Sato Y. et al. (1996) Science Vol. 273 pp. 352–354; Krieg A. M. (1996) Trends in Microbiol. 4 pp. 73–77.

The bacteriophage may also be associated with a so-called "vehicle". A vehicle is a compound, or substrate to which the bacteriophage can adhere, without being covalently bound thereto. Typical "vehicle" compounds include gold particles, silica particles such as glass and the like. Thus the bacteriophage of the invention may be introduced into an organism using biolistic methods such as the high-velocity bombardment method using coated gold particles as described in the art (Williams R. S. et al. (1991) Proc. Natl. Acad. Sci. USA 88 pp. 2726–2730; Fynan E. F. et al. (1993) Proc. Natl. Acad. Sci. USA Vol. 90 pp. 11478–11482).

In addition, the vaccine may comprise one or more suitable surface-active compounds or emulsifiers, eg. Span or Tween.

The mode of administration of the vaccine of the invention may be by any suitable route which delivers an immunoprotective amount of the virus of the invention to the subject. However, the vaccine is preferably administered parenterally via the intramuscular or deep subcutaneous routes. Other modes of administration may also be employed, where desired, such as via mucosal routes (eg. rectal, oral, nasal or vaginal administration) or via other parenteral routes, ie., intradermally, intranasally, or intravenously. Formulations for nasal administration may be developed and may comprise for example chitosan as an adjuvant (Nat. Medicine 5(4) 387–92, 1999).

It will be understood, however, that the specific dose level for any particular recipient organism will depend upon a variety of factors including age, general health, and sex; the time of administration; the route of administration; synergistic effects with any other drugs being administered; and the degree of protection being sought. Of course, the administration can be repeated at suitable intervals if necessary.

In a further aspect therefore, the present invention provides a method of immunising, prophylactically and/or therapeutically, a human or animal, comprising administering to the human and/or animal an effective dose of a vaccine formulation as described herein. It being understood that an effective dose is one which is capable of eliciting an immune response in the human and/or animal.

The present invention will now be further described by way of Example and with reference to the following Figures.

EXAMPLE 1

A phage expression library was constructed by cloning semi-random fragments (Tsp509I: cuts at AATT) of the genome of Mycoplasma capricolum subspecies capripneumoniae (Mccp) strain F38 into the EcoRI site of the lambda ZAP express expression vector (made by Stratagene). This phage contains a cytomegalovirus promoter sequence, and a LacZ promoter so inserts can be expressed in both prokaryotic and eukaryotic cells.

The test "library" used, based upon mycoplasmal DNA is likely to give poorer results compared to more suitable constructs, and results obtained should be interpreted in the light of this. It is very likely that a more suitable library construct would gave vastly better responses. Mycoplasmal DNA is very AT rich (Mccp DNA is 75% AT). Thus aberrant expression from AT-rich promoter-like sequences is likely to occur at a high frequency. In addition, codon usage of mycoplasmal DNA is unusual; the codon for tryptophan is UGA, which is a "stop" codon for most other prokaryotic and eukaryotic organisms. Hence any proteins containing tryptophan will not be expressed properly. Additionally, the present example is based on a whole unfractionated library. This includes intergenic (non-coding regions). Moreover, only 1:6 of the inserts will be in the correct orientation to given expression. For all these reasons it is clear that the vast majority of constructs in the library will result in no protein (antigen) expression following "DNA " vaccination.

Large-scale cultures of phage were grown on agar plates, harvested and the phage particles purified and concentrated by a, combination of precipitation with polyethylene glycol and ultracentrifugation (Sambrook J, et al. 1989, Molecular cloning: a laboratory manual. Cold Spring Harbor Laboratory Press, N.Y.). Half of the phage suspension was directly used to inoculate one group of mice ("Phage" DNA vaccine). DNA was extracted from the other half of the phage suspension and used to inoculate a second group of mice ("Naked" DNA vaccine).

Sixteen mice were injected intramuscularly with 25 μl phage containing the cloned F38 library at 4×10$^{11}$ particles/ml mixed with 25 μl montanide ISA 206 adjuvant. A sample of this immunogen was titred and plated out on a lawn of E. coli to ensure that addition of montanide has not in any way damaged the phage particles. A second set of sixteen mice were similarly injected with 0.5 μg of the extracted DNA (equivalent to the amount of DNA contained within the whole phage injection) in a total volume of 50 μl SM buffer. DNA was purified using Wizard lambda preps (Promega). A group of 8 mice were injected with purified C1857 phage in the manner described for the phage library. This is also a lambda phage and was used as a negative control.

Mice were pre-bled before being inoculated on day 0. On day 34 an identical booster injection was given. On day 72 the mice were challenged with whole mycoplasma, before being exsanguinated on day 83. Test bleeds were taken every two weeks, until the conclusion of the experiment. Bleeds were tested by ELISA against whole cells of Mycoplasma capricolum strains F38. In both the "Naked" DNA control and negative phage (cI857) control groups, no significant response was observed until the final injection containing whole cells. By contrast, mice inoculated with the phage library showed a significant positive response before the final injection was given (FIG. 1). In addition, the relative amount of the different subtypes of immunoglobulin present in the final bleed was examined. It was found that in the mice vaccinated with the phage library the relative concentration of IgG to IgM was significantly higher (FIG. 2). High levels of IgG are indicative of a secondary response, whereas IgM is indicative of a primary response.

EXAMPLE 2

The uptake of phage particles directly by antigen presenting cells was also examined. In this instance the whole λ Mccp library was not used. Instead, a phage clone was picked which gave a good positive response against polyclonal rabbit Mccp antiserum when plated on E. coli (protein expression was induced using IPTG). The clone was amplified and purified. DNA was also extracted from this phage as previously described. Samples of DNA and whole phage particles of this clone were added to cultures of mouse peritoneal macrophages. To extract macrophage, 2 mice were injected intraperitoneally with 2 ml of thioglycollate medium. 5 days later the mice were killed and the peritoneal cavity lavaged with 2 ml of magnesium/calcium free Hanks buffered salt solution (HBSS) These extracted cells were pelleted and washed twice in HBSS and a viable count performed in the presence of trypan blue. 10$^6$ macrophage were incubated at 37° C. in 1 ml RPMI containing 10% foetal bovine serum (FBS) for 2 h in 24 well microtitre plates to allow them to adhere. The supernatant containing non-adherent cells was removed and fresh medium added. 10$^9$ phage particles of this particular clone were added to one well and 50 ng of DNA was extracted from this clone and added to fresh medium and cultured overnight at 37° C. Phage containing no insert and DNA extracted from these "no-insert" phage were used as negative controls.

After incubation the macrophage were placed at 4° C. to detach from the microtitre plate, before they were harvested and washed in HBSS. $10^5$ cells were then spun onto a glass slide and a cytostain performed using rabbit Mccp polyclonal antiserum. The purified IgG fractioned was used. This antiserum was not further purified (ie. it was a polyvalent antiserum raised against whole Mccp, and thus recognises a broad range of Mccp proteins and other contaminants. As such, the signal to noise ratio is likely to be much lower than would be expected for a monovalent serum or a monoclonal antibody raised against the particular clone under test). A secondary biotinylated antibody (goat anti rabbit whole immunoglobulin) along with an avidin/biotin/peroxidase DAB based system was used to visualise expressed protein.

Although high backgrounds were observed (probably due to the use of a non-specific polyclonal primary antibody, and the use of a secondary antibody raised against whole rabbit immunoglobulin rather than the IgG fraction) more intense, specific staining was observed in the cell cultures spiked with insert-containing phage when compared to the negative controls (FIG. 3).

EXAMPLE 3

A different expression library was tested, and modified vaccination conditions were examined. A phage expression library was constructed by cloning semi-random fragments (Tsp509I: cuts at AATT) of the genome of *Mycoplasma mycoides* subspecies *mycoides* small colony biotype (MmmSC) strain $T_1$44 into the EcoRI site of the lambda ZAP expression vector. The vector system, cloning and phage purification procedure followed were similar to those described in Example 1, although some differences in procedure occurred during the vaccination phase (route of administration, presence of adjuvant, immunisation schedule). Ten mice per group were tested (BALB/C strain, specified pathogen free, age 10–12 weeks). Mice were injected subcutaneously (without adjuvant) with 50 μl phage containing the MmmSC library at $1.7\times10^{11}$ particles per ml. Control mice were not injected. Mice were pre-bled before being vaccinated on day 0. On day 28 an identical booster injection was given. Test bleeds were taken on Day 0, 21, and 42. Bleeds were tested by ELISA against sonicated whole cell extracts of MmmSC strain $T_1$44. None out of 10 control (non-immunised) mice showed an immune response. Two out of 10 mice immunised with the whole MmmSC expression library showed a significant immune response, while two others showed a lower level response (FIG. 4).

EXAMPLE 4

A DNA construct expressing a specific antigen (green fluorescent protein [GFP]) was used to vaccinate mice and the immune response was measured. The vaccine antigen was presented to the immune system either as purified plasmid DNA pEGFP-C1 ("naked" DNA) or as a bacteriophage GFP vaccine (λ-GFP). λ-GFP was constructed from the plasmid pEGFP-C1 (Clonetech, catalogue no. 6084-1) and NM459 (obtained from Noreen Murray). NM459 is a $cI^{857}$ nin derivative of phage construct XII from: Murray and Murray (1974). Manipulation and restriction targets in phage λ to form receptor chromosomes for DNA fragments. Nature, 251 p476–481.

pEGFP-C1 DNA was digested with EcoRI and the enzyme heat inactivated before extraction with phenol: chloroform: isoamyl alcohol and ethanol precipitation. NM459 DNA was also extracted and digested with EcoRI. The restriction enzyme was then heat inactivated and the fragment dephosphorylated (with calf intestinal alkaline phosphatase) to prevent self-ligation during subsequent steps. This enzyme was then also heat inactivated and the DNA extracted with phenol: chloroform: isoamyl alcohol and ethanol precipitated. These fragments were then ligated and the cloned DNA packaged in vitro using a Promega Packagene Lambda DNA packaging system (Cat no. K3154).

After packaging 6 clones were picked from LB-agar plates. These were amplified, DNA was extracted and digested with EcoRI to confirm the presence of the insert. One of these clones was then amplified on a larger scale and concentrated stocks prepared for vaccination of mice.

Mice were strain C57, 8–10 weeks of age, 8 mice per group. Group 1 was injected intramuscularly on day 0 and day 14 with 1 μg of plasmid DNA (pEGFP-C1) in 0.1 ml of T.E. buffer. Group 2 were injected intramuscularly on day 0 and day 14 with 50 μl of λ-GFP at $10^{11}$ particles per ml. Mice were bled on day 0 (prior to vaccination), day 14 (prior to the second vaccination), and day 28. Bleeds were tested by immunoblotting to detect a size-specific immune response against recombinant GFP, obtained from Clontech, Cat. No. 8360-2 (FIG. 5A) or bacteriophage λ proteins (FIG. 5B). Two out of 8 mice vaccinated with λ-GFP showed a strong immune response against GFP (at day 28 (FIG. 5A). Another mouse showed a response at day 14 which was lost by day 28 (data not shown); it is possible that the day 14 and day 28 samples for this mouse became mixed up. Of the group vaccinated with plasmid pEGFP-C1, only 1 animal showed a response against GFP. The signal was much weaker than the signal seen from the two positive animals which had been vaccinated with λ-EGFP. All mice vaccinated with λ-EGFP showed a strong immune response against bacteriophage λ proteins at days 14 and 28, while none of the mice vaccinated with plasmid pEGFP-C1 showed a response (FIG. 5B. Only bleeds from some animals are shown since identical results were observed with all animals from both groups).

EXAMPLE 5

The uptake of phage particles directly by antigen presenting cells was also examined. Plasmid pEGFP-C1 was also tested as a control. For this experiment λ-GFP (described in Example 3) and another construct, λB1 were tested. λB1 was isolated from the λ MmmSC expression library described in Example 3. λB1 contained the pyruvate dehydrogenase (pdh) gene of MmmSC (encoding a protein of 55 kD) and several other unidentified open reading frames. When this clone was excised as a plasmid and transformed into *Escherichia coli*, two proteins were identified when these cell extracts were run out on SDS-PAGE gels, transferred to nitrocellulose and probed with rabbit hyperimmune antiserum raised against MmmSC. The molecular weights of these two proteins were 55 kD and 29 kD, and they were not observed using control *Escherichia coli* extracts (containing the plasmid only, without the pdh insert), or when *Escherichia coli* pdh-plasmid containing extracts were probed with control rabbit antiserum.

Samples of plasmid DNA and whole phage particles of these clones were added to cultures of mouse peritoneal macrophages. To extract the macrophages, 2 mice were injected intraperitoneally with 2 ml of thioglycollate medium. Five days later the mice were killed and the peritoneal cavity lavaged with 2 ml of magnesium/calcium free Hanks buffered salt solution (HBSS). These extracted cells were pelleted and washed twice in HBSS and a viable count performed in the presence of trypan blue. $10^6$ macrophage were incubated at 37° C. in 1 ml serum free RPMI for 2 h in 24 well microtitre plates to allow them to adhere. The supernatant containing non-adherent cells was removed, the adherent cells were washed twice in PBS at 37° C., and 1 ml RPMI containing 10% foetal bovine serum (FBS) added. $10^9$ phage particles of clones λ-GFP and λ B1 were added to individual wells, or alternatively, 100 ng of purified plasmid pEGFP-C1 in T.E. buffer was added. The cells were overlaid with fresh medium and cultured overnight at 37° C.

After incubation the macrophage were placed at 4° C. for 1 h to allow them to detach from the microtitre plate before they were harvested and washed in HBSS. $5 \times 10^5$ cells were then spun onto a glass slide and a cytostain performed using either rabbit MmmSC polyclonal antiserum, 1:1000 dilution in PBS (purified IgG fractioned), or rabbit GFP polyclonal antiserum, 1:5000 dilution (obtained from Invitrogen, Cat. No. R970-01). Neither antiserum was affinity purified against GFP or the MmmSC pdh gene product, and therefore might be expected to give a relatively high background. A secondary biotinylated antibody (goat anti rabbit whole immunoglobulin) along with an avidin/biotin/peroxidase DAB based system was used to visualise expressed protein.

Figure 6B:
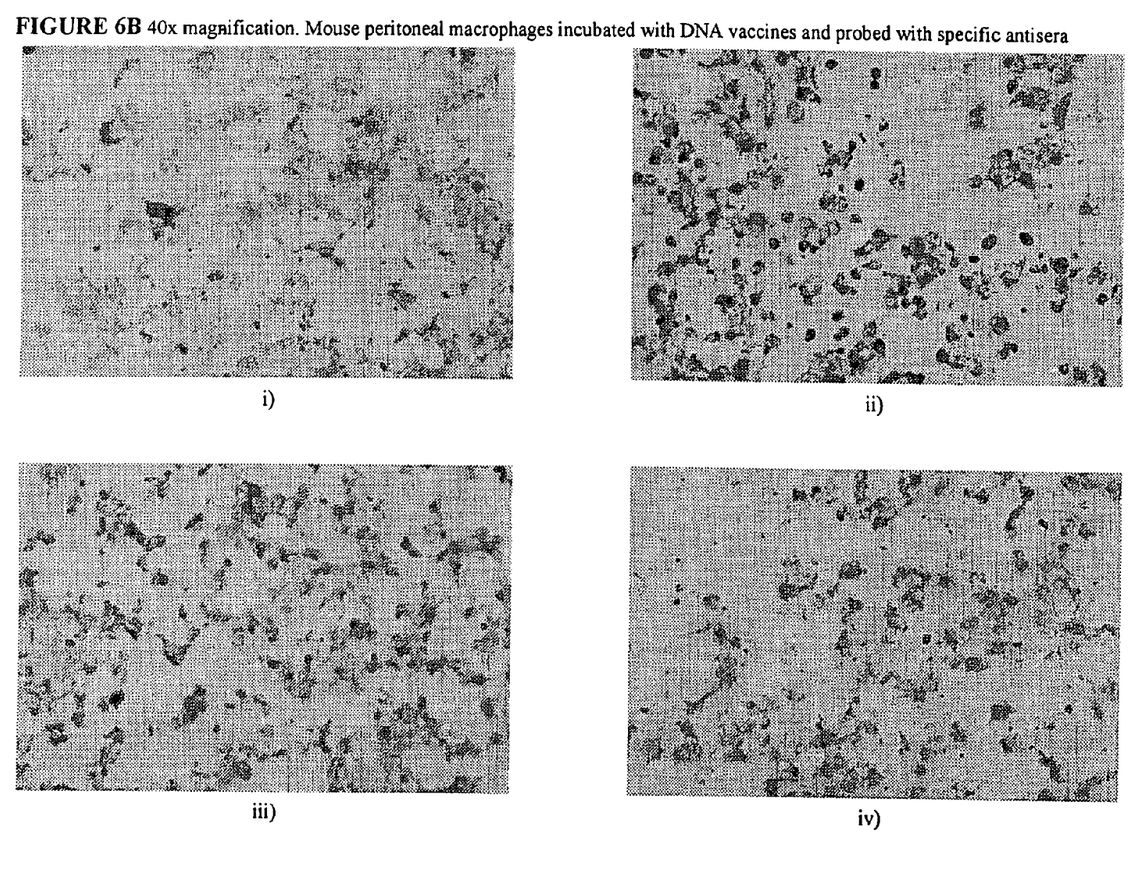
Figure 7:
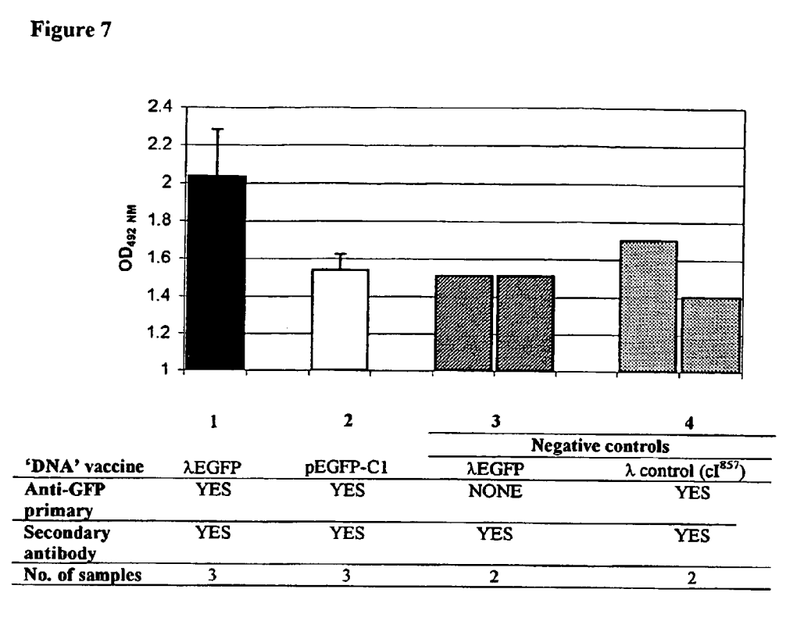
FIG. 7 ELISA measure of anti-GFP signal from macrophages incubated with λEGFP, pEGFP-Cl or a non-expressing λ control (λcI$^{857}$). Three separate assays were run for macrophages incubated with λEGFP (1) or pEGFP-Cl (2) and the mean values and standard deviations of the anti-GFP signals are shown. Two separate assays were run for the negative controls, these are plotted individually. Assay (3) shows the secondary antibody only signal against λEGFP, which assay (4) shows the non-specific signal from both primary and secondary antibodies against bacteriophage λ proteins.

Although some background signals were observed (probably due to the use of a non-specific polyclonal primary antibody, and the use of a secondary antibody raised against whole rabbit immunoglobulin rather than the IgG fraction), more intense, specific staining was observed in the cell cultures spiked with insert-containing phage (GFP and B1) when compared to the controls (FIG. 6A at 10× magnification, and FIG. 6B, 40× magnification). This staining was more noticeable with colour plates due to the difference in signal between the specific brown staining of the peroxidase/DAB system seen with a positive signal, as compared to the general violet staining of the macrophages. To confirm that staining was not due to antiserum binding to the bacteriophage lamba particles or pEGFP-C1 DNA that were added to the macrophages prior to visualisation, the following experiment was conducted. Phage particles ($10^9$) or pEGFP-C1plasmid DNA (500 ng) were spotted onto a nitrocellulose filter, and incubated with the same primary and secondary antiserum used in the experiments shown in FIGS. 6A and 6B. When developed using the same procedure, no staining was seen, indicating that any signal observed in thse figures could not be due to non-specific binding of the antiserum to either bacteriophage λ or plasmid DNA.

EXAMPLE 6

The uptake of phage particles and expression of vaccine antigen directly by antigen presenting cells was also examined using a quantitative ELISA system. For this experiment λ-GFP (described in Examples 4 and 5) and plasmid pEGFP-C1 were tested. A standard non-expressing bacteriophage λ construct was also tested as a negative control (λ-cI$^{857}$). Macrophage (as described in Example 4) were removed from liquid nitrogen, washed twice in serum/antibiotic-free RPMI medium, resuspended in the same medium and $10^6$ cells per well added to the wells of a 96 well culture plate. Macrophage were then incubated at 37° C. for 2 hours to allow the cells to attach, before the medium was removed and 100 μl fresh RPMI (containing 10% fetal calf serum+antibiotics) was added to each well. $10^9$ phage (either λEGFP or negative control λ-cI$^{857}$) or 50 ng pEGFP-C1 DNA were added per test well. The test plate was then incubated at 37° C. overnight with 5% $CO_2$.

After incubation wells were washed four times in PBS, and antigen production was measured by ELISA using a Vector labs ABC biotin/avidin detection system (Cat. No. PK-6200). Primary antiserum was rabbit anti-GFP (Invitrogen). Bound secondary antibody was quantified using SIGMA O-phenylenediamine dihydrochloride tablets (Cat. No. P-9187). Results were read in the culture plates at 492 nm and are shown in FIG. 6. The mean ELISA value observed for macrophages given λ EGFP was 2.03±0.25, significantly higher than that observed for macrophages given pEGFP-C1 (mean value 1.54±0.08, p<0.05). The value observed with pEGFP-C1 was not obviously higher than that observed with the two negative control assays, although since these were only performed in duplicate a statistical comparison is not possible.

The invention claimed is:

1. An immunogenic formulation consisting essentially of a pharmaceutically acceptable carrier and a bacteriophage particle comprising an exogenous nucleic acid under the control of a eukaryotic promoter, wherein the exogenous nucleic acid encodes a polypeptide which is capable of expression and presentation on the surface of an antigen presenting cell of an organism such that an immune response to the polypeptide is raised in the organism, said polypeptide is not designed to target the phage to receptors on the surface of specific cell types, and said bacteriophage has been modified to present said polypeptide on the surface of the phage particle.

2. The formulation according to claim 1, wherein the polypeptide elicits an immune response against a virus, bacterium, fungus, yeast, protozoan, helminth, insect or transmissible spongiform encephalopathy.

3. The formulation according to claim 1, wherein the polypeptide elicits an immune response against a cancer cell specific antigen.

4. The formulation according to claim 1, wherein the bacteriophage comprises transcriptional and/or translational regulators to facilitate expression of the polypeptide in addition to a eukaryotic promoter.

5. The formulation according to claim 1, wherein the eukaryotic promoter is selected from the group consisting of a CMV, SV40, thymidine kinase and RSV promoter.

6. The formulation according to claim 1, wherein the eukaryotic promoter is a constitutive promoter.

7. The formulation according to claim 1, wherein the eukaryotic promoter is a controllable promoter.

8. The formulation according to claim 1, wherein the bacteriophage is lambda (λ), pl phage, T phage, Mu, fd, M13 or a filamentous phage.

9. The formulation according to claim 1, wherein the bacteriophage is abortive to lytic growth in the natural bacterial flora of the chosen mammalian host.

10. The formulation according to claim 1, further comprising inhibitors of lysosomal/endosomal enzymic catabolism and/or nuclear localization signals.

11. The formulation according to claim 1, further comprising an adjuvant.

12. The formulation according to claim 1, wherein the bacteriophage is associated with a vehicle.

13. An immunogenic formulation consisting essentially of (A) a pharmaceutically acceptable carrier, (B) a bacteriophage particle comprising an exogenous nucleic acid under the control of a eukaryotic promoter, wherein the exogenous nucleic acid encodes a polypeptide which is capable of expression and presentation on the surface of an antigen presenting cell of an organism such that an immune response to the polypeptide is raised in the organism, and the surface of the bacteriophage particle has not been modified to present an exogenous peptide or protein designed to target the phage to receptors on the surface of specific cell types, and (C) an amount of the polypeptide encoded by the exogenous nucleic acid.

14. An immunogenic formulation consisting essentially of a pharmaceutically acceptable carrier and a bacteriophage particle comprising an exogenous nucleic acid under the control of a eukaryotic promoter, wherein the exogenous nucleic acid encodes a polypeptide which is capable of expression and presentation on the surface of an antigen presenting cell of an organism such that an immune response to the polypeptide is raised in the organism, the exogenous nucleic acid further encodes a polypeptide capable of augmenting the immune response, and the surface of the bacteriophage particle has not been modified to present an exogenous peptide or protein designed to target the phage to receptors on the surface of specific cell types.

15. A method of treating disease in a human or animal organism consisting essentially of administering an immunologically effective amount of a formulation consisting essentially of a pharmaceutically acceptable carrier and a bacteriophage particle comprising an exogenous nucleic acid under the control of a eukaryotic promoter, wherein the exogenous nucleic acid encodes a polypeptide which is capable of expression and presentation on the surface of an antigen presenting cell of the organism such that an immune response to the polypeptide is raised in the organism, and the surface of the bacteriophage particle has not been modified to present an exogenous peptide or protein designed to target the phage to receptors on the surface of specific cell types.

16. A method of treating disease according to claim 15, wherein the disease is an infectious disease.

17. A method of ameliorating disease in a human or animal organism consisting essentially of administering an immunologically effective amount of a formulation consisting essentially of a pharmaceutically acceptable carrier and a bacteriophage particle comprising an exogenous nucleic acid under the control of a eukaryotic promoter, wherein the exogenous nucleic acid encodes a polypeptide which is capable of expression and presentation on the surface of an antigen presenting cell of the organism such that an immune response to the polypeptide is raised in the organism, and the surface of the bacteriophage particle has not been modified to present an exogenous peptide or protein designed to target the phage to receptors on the surface of specific cell types.

18. A method of raising an immune response in a human or animal organism consisting essentially of administering an immunologically effective amount of a formulation consisting essentially of a pharmaceutically acceptable carrier and a bacteriophage particle comprising an exogenous nucleic acid under the control of a eukaryotic promoter, wherein the exogenous nucleic acid encodes a polypeptide which is capable of expression and presentation on the surface of an antigen presenting cell of the organism such that an immune response to the polypeptide is raised in the organism, and the surface of the bacteriophage particle has not been modified to present an exogenous peptide or protein designed to target the phage to receptors on the surface of specific cell types.

* * * * *